(12) United States Patent
Hancock et al.

(10) Patent No.: US 12,082,866 B2
(45) Date of Patent: Sep. 10, 2024

(54) ELECTROSURGICAL INSTRUMENT

(71) Applicant: CREO MEDICAL LIMITED, Chepstow (GB)

(72) Inventors: Christopher Paul Hancock, Bath (GB); Patrick Burn, Chepstow (GB); Pallav Shah, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 662 days.

(21) Appl. No.: 17/058,042

(22) PCT Filed: May 24, 2019

(86) PCT No.: PCT/EP2019/063488
§ 371 (c)(1),
(2) Date: Nov. 23, 2020

(87) PCT Pub. No.: WO2019/228927
PCT Pub. Date: Dec. 5, 2019

(65) Prior Publication Data
US 2021/0196376 A1 Jul. 1, 2021

(30) Foreign Application Priority Data

May 30, 2018 (GB) ...................................... 1808810

(51) Int. Cl.
*A61B 18/12* (2006.01)
*A61B 1/005* (2006.01)
(Continued)

(52) U.S. Cl.
CPC .......... *A61B 18/1206* (2013.01); *A61B 1/005* (2013.01); *A61B 1/018* (2013.01);
(Continued)

(58) Field of Classification Search
CPC . A61B 18/1815; A61B 18/1492; A61B 18/16; A61B 18/1206; A61B 18/14;
(Continued)

(56) References Cited

U.S. PATENT DOCUMENTS

| 5,904,709 A * | 5/1999 | Arndt ................. A61B 18/1815 |
| | | 607/101 |
| 2007/0043346 A1 * | 2/2007 | Cronin ................. A61B 18/18 |
| | | 607/101 |

(Continued)

FOREIGN PATENT DOCUMENTS

| EP | 2 361 581 A1 | 3/2011 |
| GB | 2486343 A | 6/2012 |

(Continued)

OTHER PUBLICATIONS

International Preliminary Report on Patentability issued from the International Preliminary Examining Authority in counterpart International Application No. PCT/EP2019/063488, mailed on Sep. 25, 2020.

(Continued)

*Primary Examiner* — Khadijeh A Vahdat
*Assistant Examiner* — Marina Delaney Templeton
(74) *Attorney, Agent, or Firm* — ArentFox Schiff LLP

(57) ABSTRACT

An electrosurgical instrument for delivering both microwave and radiofrequency (RF) energy in which a pair of longitudinally spaced electrodes are combined with an intermediate tuning element to enable both effective bipolar RF ablation and/or coagulation and microwave ablation with a field shape that is constrained around the instrument tip. The instrument comprises a radiating tip disposed at a distal end of a coaxial cable. The tip has a distal electrode and a proximal electrode disposed on a surface of a dielectric body and physically separated by an intermediate portion of the (Continued)

dielectric body. A tuning element is mounted in the intermediate portion.

17 Claims, 6 Drawing Sheets

(51) Int. Cl.
*A61B 1/018* (2006.01)
*A61B 18/00* (2006.01)
*A61B 18/14* (2006.01)
*A61B 18/16* (2006.01)
*A61B 18/18* (2006.01)

(52) U.S. Cl.
CPC .......... *A61B 18/1492* (2013.01); *A61B 18/16* (2013.01); *A61B 18/1815* (2013.01); *A61B 2018/00077* (2013.01); *A61B 2018/00083* (2013.01); *A61B 2018/00482* (2013.01); *A61B 2018/00541* (2013.01); *A61B 2018/00577* (2013.01); *A61B 2018/00589* (2013.01); *A61B 2018/00601* (2013.01); *A61B 2018/00982* (2013.01); *A61B 2018/00994* (2013.01); *A61B 2018/1861* (2013.01)

(58) Field of Classification Search
CPC ............ A61B 18/18; A61B 2018/1876; A61B 2018/126; A61B 2018/00077; A61B 2018/00994; A61B 2018/00577; A61B 2018/00589; A61B 2018/00601; A61B 2018/1892; A61B 2018/147; A61B 2018/183; A61B 2018/1853; A61B 2018/1838
See application file for complete search history.

(56) References Cited

U.S. PATENT DOCUMENTS

| | | | | |
|---|---|---|---|---|
| 2010/0268217 | A1* | 10/2010 | Habib | A61B 18/1492 606/33 |
| 2012/0203217 | A1* | 8/2012 | Brannan | A61B 18/1815 606/33 |
| 2013/0267943 | A1* | 10/2013 | Hancock | H05B 6/806 606/33 |
| 2013/0289557 | A1* | 10/2013 | Hancock | H01Q 13/08 606/33 |
| 2015/0196350 | A1 | 7/2015 | Carmel et al. | |
| 2015/0313670 | A1 | 11/2015 | Shroff et al. | |
| 2016/0262832 | A1* | 9/2016 | Cronin | A61B 18/1815 |
| 2016/0374743 | A1* | 12/2016 | Beasley | A61B 18/1492 606/27 |

FOREIGN PATENT DOCUMENTS

| | | |
|---|---|---|
| GB | 2487199 A | 7/2012 |
| GB | 2543509 A | 4/2017 |
| GB | 2550414 A | 11/2017 |
| GB | 2569812 A | 7/2019 |
| JP | 2011-251116 A | 12/2011 |
| WO | WO2010/048335 A1 | 4/2010 |
| WO | WO2016/081650 A1 | 5/2016 |
| WO | WO2017/008020 A1 | 1/2017 |
| WO | WO2017/174513 A1 | 10/2017 |
| WO | WO2017/202737 A1 | 11/2017 |

OTHER PUBLICATIONS

International Search Report and Written Opinion, issued by International Searching Authority in corresponding International Application No. PCT/EP2019/063488, mailed on Jul. 25, 2019.
Search Report under Section 17(5), issued by the United Kingdom Intellectual Property Office in counterpart United Kingdom Application No. GB1808810.4, dated Nov. 21, 2018.
Written Opinion of the International Preliminary Examining Authority, issued by the International Preliminary Examining Authority in corresponding International Application No. PCT/EP2019/063488, mailed on May 11, 2020.

* cited by examiner

ELECTROSURGICAL INSTRUMENT

CROSS-REFERENCE TO RELATED APPLICATIONS

This application is a National Stage entry of International Application No. PCT/EP2019/063488, filed on May 24, 2019, which claims priority to British Patent Application No. 1808810.4, filed on May 30, 2018. The disclosures of the priority applications are hereby incorporated in their entirety by reference.

FIELD OF THE INVENTION

The invention relates to an electrosurgical instrument for delivering microwave energy and/or radiofrequency energy to biological tissue in order to ablate the target tissue. The probe may be inserted through a channel of an endoscope or catheter, or may be used in laparoscopic surgery or open surgery. The instrument may be used in pulmonary or gastrointestinal applications, but is not limited to such.

BACKGROUND TO THE INVENTION

Electromagnetic (EM) energy, and in particular microwave and radiofrequency (RF) energy, has been found to be useful in electrosurgical operations, for its ability to cut, coagulate, and ablate body tissue. Typically, apparatus for delivering EM energy to body tissue includes a generator comprising a source of EM energy, and an electrosurgical instrument connected to the generator, for delivering the energy to tissue. Conventional electrosurgical instruments are often designed to be inserted percutaneously into the patient's body. However, it can be difficult to locate the instrument percutaneously in the body, for example if the target site is in a moving lung or a thin walled section of the gastrointestinal (GI) tract. Other electrosurgical instruments can be delivered to a target site by a surgical scoping device (e.g. an endoscope) which can be run through channels in the body such as airways or the lumen of the oesophagus or colon. This allows for minimally invasive treatments, which can reduce the mortality rate of patients and reduce intraoperative and postoperative complication rates.

Tissue ablation using microwave EM energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating.

This principle is harnessed in microwave ablation therapies, where water molecules in target tissue are rapidly heated by application of a localised electromagnetic field at microwave frequencies, resulting in tissue coagulation and cell death. It is known to use microwave emitting probes to treat various conditions in the lungs and other organs. For example, in the lungs, microwave radiation can be used to treat asthma and ablate tumours or lesions.

RF EM energy can be used for cutting and/or coagulation of biological tissue. The method of cutting using RF energy operates based on the principle that as an electric current passes through a tissue matrix (aided by the ionic contents of the cells, i.e. sodium and potassium), the impedance to the flow of electrons across the tissue generates heat. When a pure sine wave is applied to the tissue matrix, enough heat is generated within the cells to vaporise the water content of the tissue. There is thus a large rise in the internal pressure of the cell that cannot be controlled by the cell membrane, resulting in the cell rupturing. When this occurs over a wide area it can be seen that tissue has been transected.

RF coagulation operates by applying a less efficient waveform to the tissue, whereby instead of being vaporised, the cell contents are heated to around 65° C. This dries out the tissue by desiccation and also denatures the proteins in the walls of vessels and the collagen that makes up the cell wall. Denaturing the proteins acts as a stimulus to a coagulation cascade, so clotting is enhanced. At the same time, collagen in the cell wall is denatured from a rod like molecule to a coil, which causes the vessel to contract and reduce in size, giving the clot an anchor point, and a smaller area to plug. Known systems for cutting or coagulating tissue using RF energy often involve inserting a needle electrode into target tissue in the patient, and placing a return electrode on a skin surface of the patient. The first electrode and the return electrode are both connected to an RF signal generator. RF energy may then be applied to the first electrode, which may cause heating and ablation/coagulation of the target tissue. The return electrode provides a return path for the RF energy to remove stray RF energy from the patient's body.

SUMMARY OF THE INVENTION

At its most general, the invention provides an electrosurgical instrument for delivering both microwave and radiofrequency (RF) energy in which a pair of longitudinally spaced electrodes are combined with an intermediate tuning element to enable both effective bipolar RF ablation and/or coagulation and microwave ablation with a field shape that is constrained around the instrument tip.

The electrosurgical instrument may be used to cut and/or ablate biological tissue using both RF and microwave energy. The RF energy and microwave energy may be applied separately (e.g. sequentially) or in combination. An advantage of the electrosurgical instrument of the invention is that less time may be spent on interchanging instruments during a surgical procedure, as RF and microwave energy may be applied using the same instrument, separately or simultaneously. In particular, the present invention enables a rapid change in functionality or effective treatment volume of the instrument by switching between or varying the application of RF and microwave energy.

According to a first aspect of the invention, there is provided electrosurgical instrument comprising: a coaxial feed cable for conveying microwave energy and radiofrequency energy, the coaxial feed cable having an inner conductor, an outer conductor, and a dielectric material separating the inner conductor and the outer conductor; and a radiating tip disposed at a distal end of the coaxial cable to receive the microwave energy and the radiofrequency energy, the radiating tip comprising: a longitudinally extending dielectric body; a distal electrode and a proximal electrode disposed on a surface of the dielectric body, wherein the distal electrode and the proximal electrode are physically separated from each other by an intermediate portion of the longitudinally extending dielectric body; and a tuning element mounted in the intermediate portion of the longitudinally extending dielectric body, wherein the distal electrode is electrically connected to the inner conductor, wherein the proximal electrode being electrically connected to the outer conductor, wherein the distal electrode and proximal electrode are configured as an active electrode and a return electrode for delivering the radiofrequency energy, and wherein the radiating tip is operable as an antenna (e.g. a dipole antenna) for emitting the microwave energy.

The instrument may operate to ablate target tissue in the body. The device is particularly suited to the ablation of tissue in the lungs or uterus, however it may be used to ablate tissue in other organs. In order to efficiently ablate target tissue, the radiating tip should be located as close as possible (and in many cases inside) the target tissue. In order to reach the target tissue (e.g. in the lungs), the device may need to be guided through passageways (e.g. airways) and around obstacles. This means that the instrument will ideally be as flexible as possible and have a small cross section. Particularly, the device should be very flexible near its tip, where it may need to be steered along narrow passageways such as bronchioles which can be narrow and winding.

As the proximal and distal electrodes are electrically connected to the outer and inner conductors, respectively, the proximal and distal electrodes may receive RF energy conveyed along the coaxial feed cable to serve as bipolar RF electrodes. In this manner, by conveying radiofrequency energy to the proximal and distal electrodes, biological tissue that is located between or around the electrodes may be ablated and/or coagulated. Furthermore, the longitudinal spacing between the proximal and distal electrodes enables the proximal and distal electrodes to behave as poles of a dipole antenna when microwave energy is conveyed along the coaxial feed cable. Thus, the radiating tip may behave as a microwave dipole antenna when microwave energy is conveyed along the coaxial feed cable. The spacing of the proximal and distal electrodes may depend on the microwave frequency used, and the loading caused by the target tissue.

The configuration of the radiating tip therefore enables treatment of tissue using both RF and microwave energy. In particular, the electrosurgical instrument of the invention enables emission of microwave energy from the radiating tip whilst maintaining electrical connection to the second electrode, to enable RF coagulation/ablation between the first and second electrodes. Several advantages are associated with the ability to cut and ablate tissue using both RF and microwave energy. First, time may be saved during surgical procedures, as it is not necessary to swap instruments in order to ablate tissue using RF or microwave energy. The ability to switch between RF and microwave ablation may also enable improved thermal management of the electrosurgical instrument. This is because attenuation EM energy at microwave frequencies within the coaxial feed cable may be greater than at RF frequencies. As a result, switching from microwave energy to RF energy may cause less energy to be dissipated in the coaxial feed cable, and reduce the temperature of the coaxial feed cable.

During RF tissue ablation/coagulation, a local current path may be formed between the proximal and distal electrodes (e.g. via target tissue). This may avoid the risk of skin burns that could occur at the return pad in conventional RF monopolar electrosurgical systems (e.g. due to heating at the return pad). Additionally, by creating a local current path (as opposed to using a remote return pad), the risk of injury due to stray currents in the patient's body may be reduced. The bipolar RF arrangement also reduces the risk of no or reduced energy due to a poor or high impedance contact being made to the return pad. An effect that may occur during RF tissue ablation is an increase in impedance of the target tissue due to heating in the tissue. This may reduce the effectiveness of RF ablation over time, and is known as the "drop-off" effect. By switching from RF energy delivery to microwave energy delivery, it may therefore be possible to avoid the drop-off effect, as microwave ablation may be less sensitive to temperature increases in the target tissue. The effectiveness of RF ablation may also be affected by the flow of blood or other fluids in the target tissue (perfusion), which may counteract the heating effect of the RF energy. Microwave ablation may be less susceptible to perfusion effects, such that switching from RF energy to microwave energy may enhance ablation performance where perfusion effects are a concern.

Furthermore, the inventors have found that by switching between RF energy and microwave energy, it is possible to change the radiation profile (also referred to as an "ablation profile") of the instrument. In other words, the size and shape of the volume of tissue ablated by the electrosurgical instrument may be adjusted by switching between RF energy and microwave energy. This may enable the ablation profile to be changed in situ, without having to swap instruments during a surgical procedure. This is a form of energy delivery profile control. Moreover, the combination of the physical and electrical arrangement of the proximal electrode, tuning element and distal electrode can serve to enhance the shape of the radiation profile of the microwave energy, compared to an electrosurgical instrument without the proximal and distal electrodes. In particular, the proximal and distal electrodes may act to concentrate radiated energy around the radiating tip, and reduce a radiation tail that extends along back down the coaxial feed cable.

The coaxial feed cable may be a conventional low loss coaxial cable that is connectable at one end to an electrosurgical generator. In particular, the inner conductor may be an elongate conductor extending along a longitudinal axis of the coaxial feed cable. The dielectric material may be disposed around the inner conductor, e.g. the first dielectric material may have a channel through which the inner conductor extends. The outer conductor may be a sleeve made of conductive material that is disposed on the surface of the dielectric material. The coaxial feed cable may further include an outer protective sheath for insulating and protecting the cable. In some examples, the protective sheath may be made of or coated with a non-stick material to prevent tissue from sticking to the cable. The radiating tip is located at the distal end of the coaxial feed cable, and serves to deliver EM energy conveyed along the coaxial feed cable into target tissue. The radiating tip may be permanently attached to the coaxial feed cable, or it may be removably attached to the coaxial feed cable. For example, a connector may be provided at the distal end of the coaxial feed cable, which is arranged to receive the radiating tip and form the required electrical connections.

The dielectric body may be generally cylindrical. The distal electrode and the proximal electrode may be disposed on a circumferential outer surface of the body, i.e. they are exposed on the surface of the radiating tip. The distal electrode may include a pad made of conductive material which is disposed on the surface of the radiating tip. Similarly, the proximal electrode may include a pad of conductive material which is disposed on the surface of the radiating tip. The proximal and distal electrodes may have any suitable shape, and their shape may be chosen in order to obtain a desired radiation profile of the radiating tip. The distal electrode may be directly or indirectly connected to the inner conductor. For example, the distal electrode may be connected to the inner conductor via an intermediate conductor that extends between the inner conductor and the distal electrode. Similarly, the proximal electrode may be directly or indirectly connected to the outer conductor. The outer conductor may terminate at the proximal electrode.

In some embodiments, the radiating tip may be formed by removing a portion of the outer conductor from a distal end of the coaxial feed cable. Where the proximal electrode includes a conductive ring, the conductive ring may be formed at the distal end of the outer conductor. In some examples, the conductive ring may be formed by an exposed portion of the outer conductor at its distal end.

In one example, the distal electrode may include a first conductive ring on the surface of the dielectric body. The first conductive ring may, for example, be a loop of conductive material disposed around the surface of the radiating tip. The first conductive ring may be arranged such that it is approximately centred on the longitudinal axis of the electrosurgical instrument. This may improve the symmetry of the radiation profile of the radiating tip about the longitudinal axis of the instrument. In some examples, the first conductive ring may have a cylindrical shape, e.g. it may be formed by a hollow cylindrical conductor. The cylindrical shape of the distal electrode may serve to produce a radiation profile that is symmetrical about the longitudinal axis of the instrument.

Similarly, the proximal electrode may include a second conductive ring on the surface of the dielectric body, and wherein the inner conductor is connected to the distal electrode via a conductor that passes through the second conductive ring. The second conductive ring may, for example, be a loop of conductive material disposed around the surface of the radiating tip. The second conductive ring may be arranged such that it is approximately centred on the longitudinal axis of the electrosurgical instrument. This may improve the symmetry of the radiation profile of the radiating tip about the longitudinal axis of the instrument. The second conductive ring may define a passageway through which the conductor passes to connect the inner conductor to the distal conductor.

The proximal electrode and the distal electrode may have the same dimensions. Using proximal and distal electrodes of the same length may serve to ensure that the two electrodes remain at approximately the same temperature during ablation with RF energy. This may also serve to ensure that ablation does not preferentially occur closer to one of the electrodes, so that a more uniform ablation profile may be obtained.

The longitudinal separation of the distal electrode and the proximal electrode may comprise a length of intermediate portion. Thus, the distal electrode and the proximal electrode may be electrically isolated from one another across this length. The distal electrode may be closer to a distal end of the radiating portion (e.g. closer to a distal tip of the instrument), whilst the proximal electrode may be closer to a proximal end of the radiating tip (e.g. closer to the distal end of the coaxial feed cable).

The dielectric body may comprise a protruding portion of the dielectric material of the coaxial cable that extends beyond a distal end of the outer conductor. This may simplify construction of the radiating tip, and avoid reflections of EM energy at the boundary between the radiating tip and the coaxial feed cable. In another example, a second dielectric material, different from the dielectric material of the coaxial feed cable may be used to form the dielectric body of the radiating tip. The second dielectric material may be selected to improve impedance matching with target tissue in order to improve the efficiency with which the microwave energy is delivered into target tissue. In other examples, the radiating tip may include multiple different pieces of dielectric material, which are selected and arranged to shape the radiation profile in a desired manner.

The inner conductor of the coaxial cable may extend beyond a distal end of the outer conductor through the dielectric body in order to provide an electrical connection for the distal electrode. The inner conductor may be electrically connected to the distal electrode by a conductive connection element that extends radially from the inner conductor. The conductive connection element may be a piece of conductive material that is connected (e.g. welded or soldered) between the inner conductor and the distal electrode. The conductive connection element extends laterally from the inner conductor, meaning that it extends in a direction that is angled relative to the longitudinal direction of the inner conductor (which corresponds to the longitudinal direction of the instrument). For example, the conductive connection element may be angled at 90° relative to the inner conductor. The conductive connection element may include several "branches" (e.g. wires) extending between the inner conductor and the distal electrode. The branches may be arranged symmetrically about the longitudinal axis of the instrument, to improve the axial symmetry of the instrument. In some examples, the conductive connection element may include a ring arranged around the inner conductor and connected between the inner conductor and the distal electrode, to further improve axial symmetry of the connection.

The tuning element may comprise an electrically conductive body mounted within the intermediate portion of the dielectric body, the electrically conductive body being electrically connected to the inner conductor. The tuning element may have dimensions selected to introduce a capacitance for improving the coupling efficiency of the antenna. Where the inner conductor extends into the radiating tip, the conductive tuning element may be located on the portion of the inner conductor that extends into the radiating tip. Where the inner conductor is connected to the distal electrode by an intermediate conductor, the conductive tuning element may be located on the intermediate conductor. The conductive tuning element may serve to improve the coupling efficiency of EM energy into target tissue by reducing the amount of energy reflected from the tissue. The electrically conductive body may be a sleeve mounted around a portion of the inner conductor that extends into the dielectric body.

The tuning element may have a longitudinal length less that a longitudinal separation of the distal electrode and the proximal electrode. The tuning element may be mounted within the protruding portion of the dielectric material.

The intermediate portion of the longitudinally extending dielectric body may comprise a electrically insulating collar mounted over the protruding portion of the dielectric material. The collar may be configured such that the outer surfaces of the distal electrode, intermediate portion and proximal electrode are flush along the radiating tip.

In some embodiments, the radiating tip may further include a dielectric choke. The dielectric choke may be a piece of electrically insulating material mounted with respect to the outer conductor (e.g. between the outer conductor and the proximal electrode) to reduce propagation of EM energy reflected at the radiating tip back down the coaxial feed cable. This may reduce an amount by which the radiation profile of the radiating tip extends along the coaxial feed cable, and provide an enhanced radiation profile.

The electrosurgical instrument discussed above may form part of a complete electrosurgical system. For example, the system may include an electrosurgical generator arranged to supply microwave energy and radiofrequency energy; and the electrosurgical instrument of the invention connected to receive the microwave energy and radiofrequency energy from the electrosurgical generator. The electrosurgical apparatus may further include a surgical scoping device (e.g. an endoscope) having a flexible insertion cord for insertion into a patient's body, wherein the flexible insertion cord has an instrument channel running along its length, and wherein the electrosurgical instrument is dimensioned to fit within the instrument channel.

In this specification "microwave" may be used broadly to indicate a frequency range of 400 MHZ to 100 GHz, but preferably the range 1 GHz to 60 GHz. Preferred spot frequencies for microwave EM energy include: 915 MHZ, 2.45 GHz, 3.3 GHZ, 5.8 GHz, 10 GHz, 14.5 GHZ and 24 GHz. 5.8 GHZ may be preferred. In contrast, this specification uses "radiofrequency" or "RF" to indicate a frequency range that is at least three orders of magnitude lower, e.g. up to 300 MHz. Preferably, RF energy has a frequency that is high enough to prevent nerve stimulation (e.g. greater than 10 kHz), and low enough to prevent tissue blanching or thermal spread (e.g. lower than 10 MHZ). A preferred frequency range for RF energy may be between 100 kHz and 1 MHz.

Herein, the terms "proximal" and "distal" refer to the ends of the electrosurgical instrument further from and closer to the treatment site, respectively. Thus, in use, the proximal end of the electrosurgical instrument is closer to a generator for providing the RF and/or microwave energy, whereas the distal end is closer to the treatment site, i.e. target tissue in the patient.

The term "conductive" is used herein to mean electrically conductive, unless the context dictates otherwise.

The term "longitudinal" used below refers to the direction along the length of the electrosurgical instrument, parallel to the axis of the coaxial transmission line. The term "inner" means radially closer to the centre (e.g. axis) of the instrument. The term "outer" means radially further from the centre (axis) of the instrument.

The term "electrosurgical" is used in relation an instrument, apparatus or tool which is used during surgery and which utilises microwave and/or radiofrequency electromagnetic (EM) energy.

BRIEF DESCRIPTION OF THE DRAWINGS

Examples of the invention are discussed below with reference to the accompanying drawings, in which.

It should be noted that the embodiments shown in the figures are not drawn to scale.

DETAILED DESCRIPTION; FURTHER OPTIONS AND PREFERENCES

Figure 1:
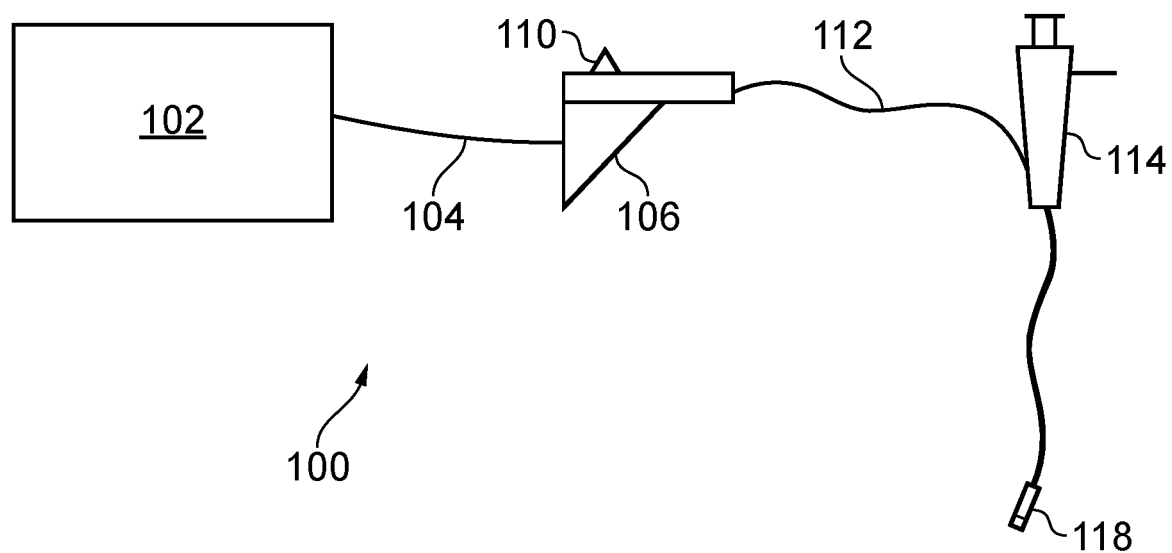
FIG. 1 is a schematic diagram of an electrosurgical system for tissue ablation that is an embodiment of the invention.

FIG. 1 is a schematic diagram of a complete electrosurgical system 100 that is capable of supplying microwave energy and radiofrequency energy to the distal end of an invasive electrosurgical instrument. The system 100 comprises a generator 102 for controllably supplying microwave and radiofrequency energy. A suitable generator for this purpose is described in WO 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level. The generator may be arranged to deliver power in a series of pulses which are modulated to match a patient's breathing cycle. This will allow for power delivery to occur when the lungs are deflated. The generator 102 is connected to an interface joint 106 by an interface cable 104. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102 and instrument control mechanism into a single flexible shaft 112, which extends from the distal end of the interface joint 106. In other embodiments, other types of input may also be connected to the interface joint 106. For example, in some embodiments a fluid supply may be connected to the interface joint 106, so that fluid may be delivered to the instrument.

The flexible shaft 112 is insertable through the entire length of an instrument (working) channel of an endoscope 114.

The flexible shaft 112 has a distal assembly 118 (not drawn to scale in FIG. 1) that is shaped to pass through the instrument channel of the endoscope 114 and protrude (e.g. inside the patient) at the distal end of the endoscope's tube. The distal end assembly includes an active tip for delivering microwave energy and radiofrequency energy into biological tissue. The tip configuration is discussed in more detail below.

The structure of the distal assembly 118 may be arranged to have a maximum outer diameter suitable for passing through the working channel. Typically, the diameter of a working channel in a surgical scoping device such as an endoscope is less than 4.0 mm, e.g. any one of 2.8 mm, 3.2 mm, 3.7 mm, 3.8 mm. The length of the flexible shaft 112 can be equal to or greater than 0.3 m, e.g. 2 m or more. In other examples, the distal assembly 118 may be mounted at the distal end of the flexible shaft 112 after the shaft has been inserted through the working channel (and before the instrument cord is introduced into the patient). Alternatively, the flexible shaft 112 can be inserted into the working channel from the distal end before making its proximal connections. In these arrangements, the distal end assembly 118 can be permitted to have dimensions greater than the working channel of the surgical scoping device 114.

The system described above is one way of introducing the instrument into a patient's body. Other techniques are possible. For example, the instrument may also be inserted using a catheter.

Figure 2:
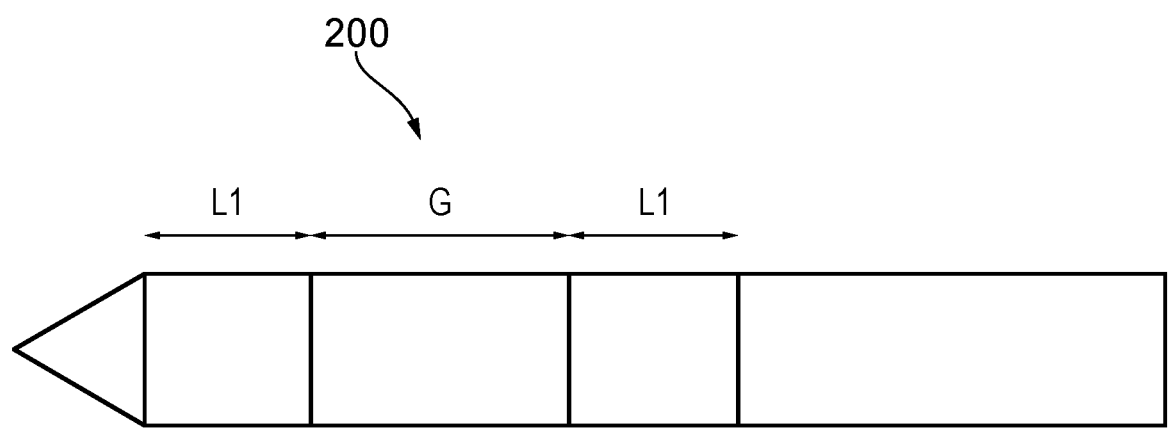
FIG. 2 is a schematic side view of an electrosurgical instrument that is an embodiment of the invention.
Figure 3:
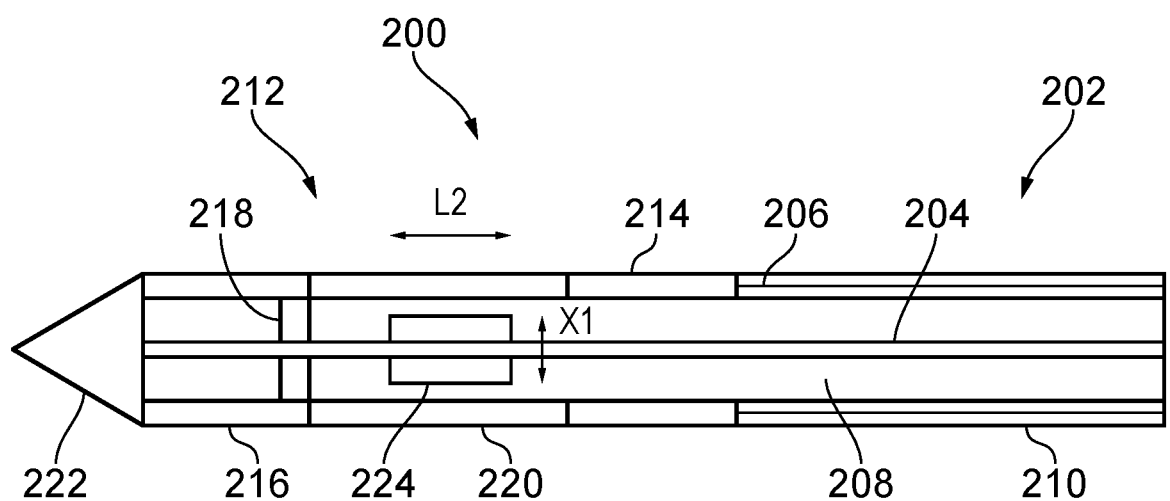
FIG. 3 is a schematic cross-sectional side view of the electrosurgical instrument of FIG. 2.

FIG. 2 is a perspective view of a distal end of an electrosurgical instrument 200 that is an embodiment of the invention. FIG. 3 shows a cross-sectional side view of the same electrosurgical instrument 200. The distal end of the electrosurgical instrument 200 may correspond, for example, to the distal assembly 118 discussed above. The electrosurgical instrument 200 includes a coaxial feed cable 202 that is connectable at its proximal end to a generator (such as generator 102) in order to convey microwave energy and RF energy. The coaxial feed cable 202 comprises an inner conductor 204 and an outer conductor 206 which are separated by a dielectric material 208. The coaxial feed cable 202 is preferably low loss for microwave energy. A choke (not shown) may be provided on the coaxial feed cable 204 to inhibit back propagation of microwave energy reflected from the distal end and therefore limit backward heating along the device. The coaxial cable further includes a flexible outer sheath 210 disposed around the outer conductor 206 to protect the coaxial cable. The outer sheath 210 may be made of an insulating material to electrically isolate the outer conductor 206 from its surroundings. The outer sheath 210 may be made of, or coated with, a non-stick material such as PTFE to prevent tissue from sticking to the instrument.

A radiating tip 212 is formed at the distal end of the coaxial feed cable 202. The radiating tip 212 is arranged to receive microwave energy and RF energy conveyed by the coaxial feed cable 202, and deliver the energy into biological tissue. The radiating tip 212 includes a proximal electrode 214 located near a proximal end of the radiating tip 212. The proximal electrode 214 is a hollow cylindrical conductor that forms an exposed ring around an outer surface of the radiating tip 212. The proximal electrode 214 is electrically connected to the outer conductor 206 of the coaxial feed cable 202. For example, the proximal electrode 214 may be welded or soldered to the outer conductor 206. The proximal electrode 214 may be electrically connected to the outer conductor 206 by a region of physical contact that extends around the whole circumference of the outer conductor 206, in order to ensure axial symmetry of the connection. The proximal electrode 214 is arranged coaxially with the coaxial feed cable 202 (i.e. the longitudinal axis of the cylindrical proximal electrode 214 is aligned with the longitudinal axis of the coaxial feed cable 202), and has an outer diameter that matches that of the coaxial feed cable 202. In this manner, the proximal electrode lies flush with the outer surface of the coaxial feed cable 202. This may prevent tissue from catching on the proximal electrode 214. The outer conductor 206 terminates at the proximal electrode 214, i.e. it does not extend beyond the proximal electrode 214 in a distal direction. In some embodiments (not shown), the proximal electrode may be an exposed distal portion of the outer conductor 206.

The radiating tip 212 also includes a distal electrode 216 located at or near a distal end of the radiating tip 212. The distal electrode 216 is a hollow cylindrical conductor that forms an exposed ring around an outer surface of the radiating tip 212. Like the proximal electrode 214, the distal electrode 216 is arranged coaxially with the coaxial feed cable 202. The proximal and distal electrodes 214, 216 may have substantially the same shape and size. As illustrated in FIG. 2, the proximal and distal electrodes 214, 216 have a length L1 in the longitudinal direction of the electrosurgical instrument 200. The distal electrode 216 is spaced apart from the proximal electrode 214 in the longitudinal direction of the electrosurgical instrument 200 by a distance G (see FIG. 2). In other words, the distal electrode 216 is further along the length of the electrosurgical instrument 200 by a distance G. The proximal and distal electrodes 214, 216 have an outer diameter which is the same as an outer diameter of the coaxial feed cable 202, so that the electrosurgical instrument 200 has a smooth outer surface.

The proximal electrode 214 (which is formed by a hollow cylindrical conductor) defines a passageway through which a distally protruding portion of the inner conductor 204 passes. In this manner, the inner conductor 204 extends into the radiating tip 212, where it is electrically connected to the distal electrode 216. The inner conductor 204 is electrically connected to the distal electrode 216 via a conductor 218 that extends radially (i.e. outwards) from the inner conductor 206. The conductor 218 may comprise one or more branches (e.g. wires or other flexible conductive elements) that are arranged symmetrically about the axis of the inner conductor 204. Alternatively, the conductor 218 may comprises a conductive disc or ring mounted around the inner conductor 204 and connected between the inner conductor 204 and the distal electrode 216. The connection between the inner conductor 204 and the distal electrode 216 is preferably symmetric around the axis defined by the inner conductor 204. This can facilitate formation of a symmetrical field shape around the radiating tip 212.

A portion of the dielectric material 208 of the coaxial feed cable 202 also extends beyond a distal end of the outer conductor 206 into the radiating tip 212 through the passageway formed by the proximal electrode 214. In this manner, the inner conductor 204 and the proximal electrode 214 are isolated by the dielectric material 208. A collar 220 is provided around the radiating tip 212 between the proximal electrode 214 and the distal electrode 216. The collar 220 may operate to protect the dielectric material 208 and ensure that the outer surface of the radiating tip is smooth. The collar 220 may be made of the same material, and serve the same function, as the outer sheath 210.

The radiating tip 212 further includes a pointed distal tip 222 located at a distal end of the instrument. The distal tip 222 may be pointed in order to facilitate insertion of the radiating tip 212 into target tissue. However, in other embodiments (not shown), the distal tip may be rounded or flat. The distal tip 222 may be made of a dielectric material, e.g. the same as dielectric material 208. In some embodiments, the material of the distal tip 222 may be selected to improve impedance matching with target tissue, in order to improve the efficiency with which the EM energy is delivered to the target tissue. The distal tip 222 may be made of, or covered with a non-stick material (e.g. PTFE) to prevent tissue from sticking to it.

The radiating tip 212 further includes a tuning element 224. The tuning element 224 is an electrically conductive element connected to the inner conductor 204 between the proximal electrode 214 and the distal electrode 216 to introduce a capacitive reactance. In this example, the conductive tuning element is cylindrically shaped, and is arranged coaxially with the inner conductor 204. The tuning element 224 has a length L2 in the longitudinal direction, and an outer diameter X1 (see FIG. 3). These parameters can be selected to introduce a capacitance that improves the coupling efficiency (i.e. reduces the reflected signal) of the instrument when operating as a microwave antenna as discussed below.

As the proximal electrode 214 and the distal electrode 216 are electrically connected to the outer conductor 206 and the inner conductor 204, respectively, they may be used as bipolar RF cutting electrodes. For example, the distal electrode 216 may act as an active electrode and the proximal electrode 214 may act as a return electrode for RF energy conveyed along the coaxial feed cable 202. In this manner, target tissue disposed around the radiating tip 212 may be cut and/or coagulated using RF energy, via the mechanisms discussed above.

Additionally, the radiating tip 212 may behave as a microwave dipole antenna, when microwave energy is conveyed along the coaxial feed cable 202. In particular, the proximal electrode 214 and the distal electrode 216 may act as radiating elements of the dipole antenna at microwave frequencies. Thus, the radiating tip structure enables both radiofrequency energy and microwave energy to be delivered into target tissue. This enables target tissue to be ablated and/or coagulated using radiofrequency and microwave energy, depending on the type of EM energy conveyed to the radiating tip. The cylindrical shapes of the proximal and distal electrodes 214, 216 may serve to produce a radiation profile that is symmetric about a longitudinal axis of the instrument 200.

The configuration of the electrodes 214, 216 determined by the parameters L1 and G can be selected in advance to provide a desired ablation diameter (for a given energy waveform and local tissue properties). Cylindrical electrodes are used to produce a symmetrical (about the longitudinal device axis) ablation profile. The following are example dimensions that can be used for an electrosurgical instrument that is an embodiment of the invention: L1 and L2 may be 3 mm; G may be 5 mm; X1 may be 1.2 mm; the outer diameter of the instrument may be approximately 1.9 mm; the inner diameter of the proximal and distal electrodes may be 1.5 mm.

Figure 4:
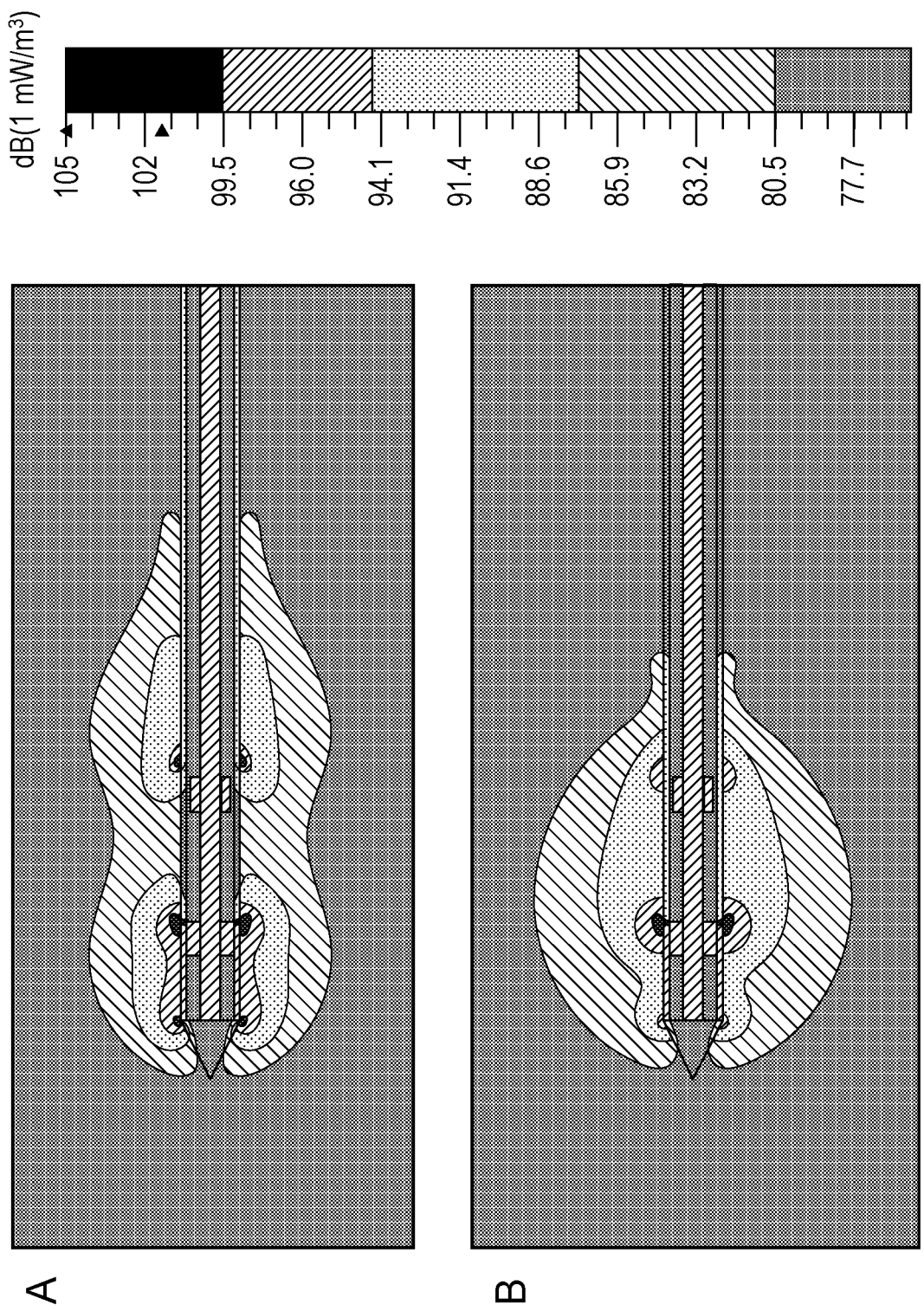
FIG. 4 is a diagram showing simulated radiation profiles for an electrosurgical instrument that is an embodiment of the invention.

FIG. 4 shows calculated radiation profiles in target tissue for an electrosurgical instrument according to an embodiment of the invention. Panel A of FIG. 4 shows a simulated radiation profile at 400 kHz (i.e. for radiofrequency energy) and panel B of FIG. 4 shows a simulated radiation profile at 5.8 GHZ (i.e. for microwave energy). As can be seen, at both frequencies, the radiation profile extends between and around the proximal and distal electrodes. The radiation profile for the microwave energy (panel B) is more spherical than for the radiofrequency energy (panel A). In contrast, the radiation profile for the radiofrequency has a more elongate shape, and is more concentrated around the proximal and distal electrodes. Therefore, the radiation profile changes depending on whether microwave energy or radiofrequency energy is conveyed to the radiating tip. This may result in a different ablation volume (i.e. a volume of target tissue that is ablated by the EM energy), depending on the type of EM energy conveyed to the radiating tip. Thus, for example, the ablation volume may be controlled by switching between microwave energy and radiofrequency energy.

Figure 5:
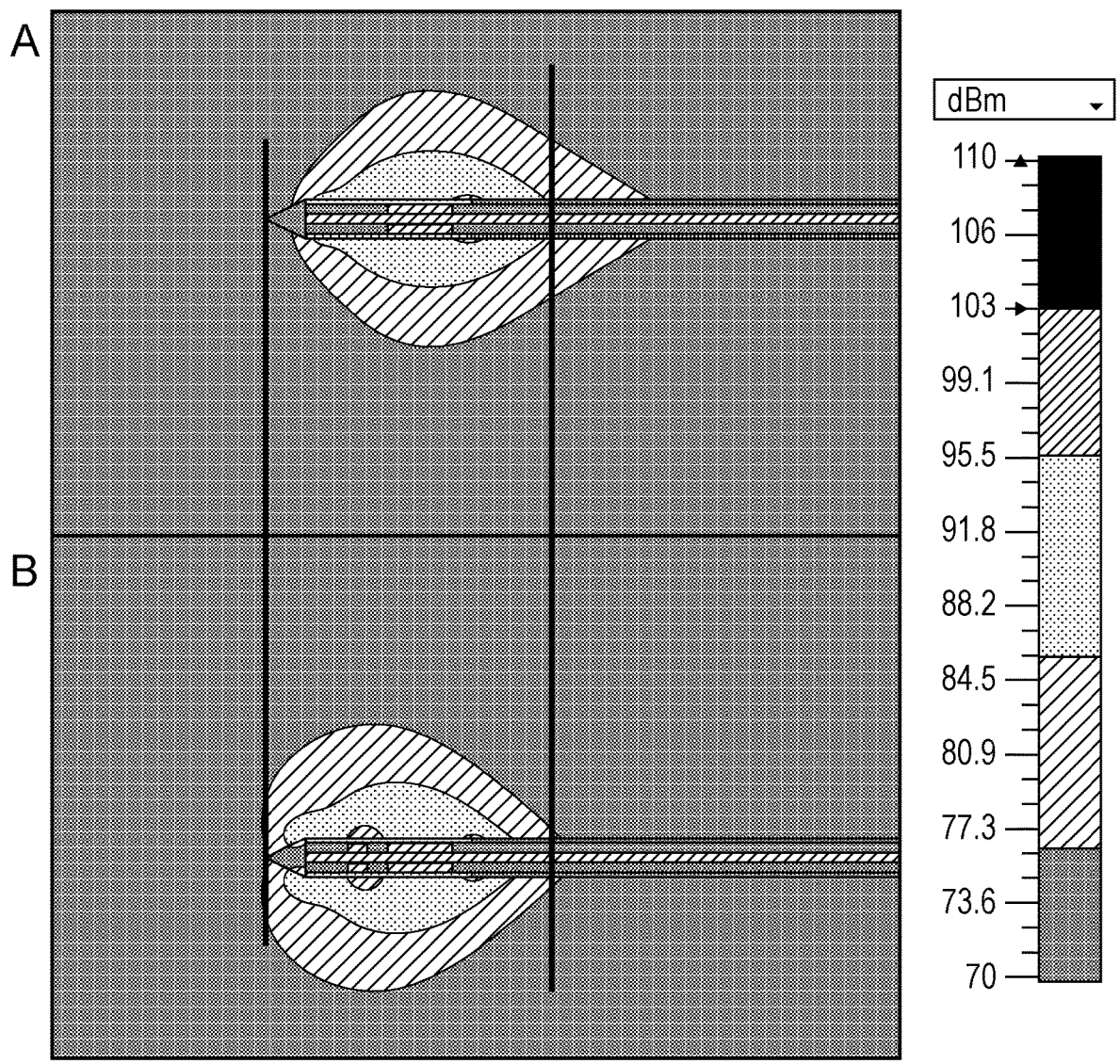
FIG. 5 is a diagram comparing simulated radiation profiles for an electrosurgical instrument that is not an embodiment of the invention and for and electrosurgical instrument that is an embodiment of the invention.
Figure 6:
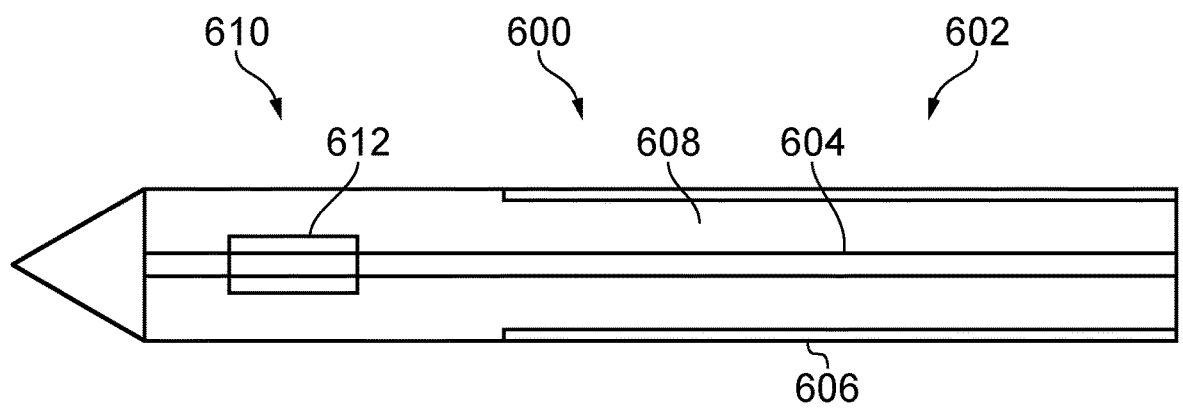
FIG. 6 is a schematic cross-section side view of an electrosurgical instrument that is not an embodiment of the invention.

FIG. 5 illustrates how the microwave radiation profile of the electrosurgical instrument is affected by the presence of the proximal and distal electrodes. Panel A of FIG. 5 shows a calculated radiation profile for an electrosurgical instrument which does not have proximal and distal electrodes. The structure of the electrosurgical instrument of Panel A of FIG. 5 is illustrated in FIG. 6. The electrosurgical instrument 600 illustrated in FIG. 6 has a similar structure to that shown in FIGS. 2 and 3, except that it does not include proximal and distal electrodes. Like the electrosurgical instrument 200 of the embodiment, electrosurgical instrument 600 includes a coaxial feed cable 602 having an inner conductor 604 and an outer conductor 606 which are separated by a dielectric material 608. A radiating tip 610 is formed at the end of the coaxial feed cable 602. The inner conductor 604 and the dielectric material extend into the radiating tip 610, however the outer conductor 606 terminates at the radiating tip 610. A conductive tuning element 612 is provided on the inner conductor in the radiating tip 610. Panel B of FIG. 5 shows a calculated radiation profile for an electrosurgical instrument having a structure according to an embodiment of the invention (e.g. similar to that shown in FIGS. 2 and 3). Both radiation profiles are simulations at a microwave energy frequency of 5.8 GHz. Except for the lack of proximal and distal electrodes in electrosurgical instrument 600, the dimensions of the electrosurgical instruments used in both simulations are the same.

As can be seen from FIG. 5, the shape of the calculated radiation profiles differs between the electrosurgical instruments. In particular, the radiation profile of the electrosurgical instrument according to the embodiment of the invention (panel B) is more spherical in shape compared to the radiation profile of electrosurgical instrument 600 (panel A). As indicated by the lines in FIG. 5, the radiation profile of the electrosurgical instrument according to the embodiment of the invention is more concentrated around the radiating tip. In contrast, the radiation profile of electrosurgical instrument 600 has a longer tail which extends along a portion of the coaxial feed cable. This extending of the radiation profile down the coaxial feed cable may be referred to as the "teardrop effect". Thus, the use of proximal and distal electrodes in the electrosurgical instrument serves to reduce the teardrop effect. The radiation profile of the electrosurgical instrument of the embodiment may be advantageous in that it may avoid ablating tissue that is located away from the radiating tip. The teardrop effect may further be reduced by including a dielectric choke in the radiating tip of the electrosurgical instrument of the embodiment. For example, the dielectric choke may be a piece of dielectric material that is located in the radiating tip, between the proximal electrode and the outer conductor (i.e. in the passageway defined by the proximal electrode).

Figure 7:
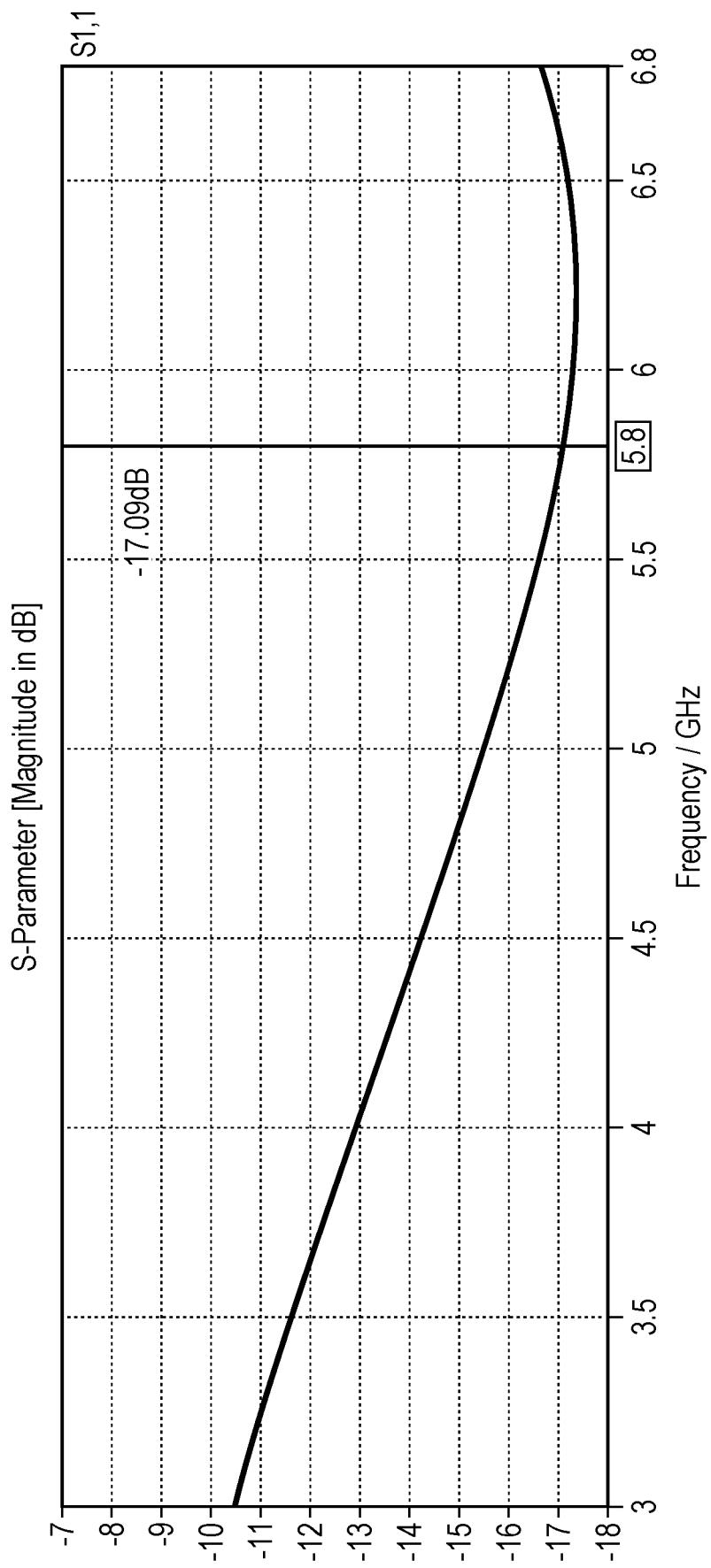
FIG. 7 is a plot of the simulated return loss for an electrosurgical instrument that is an embodiment of the invention.

FIG. 7 shows a simulated plot of the S-parameter (also known as the "return loss") against frequency of the microwave energy for the electrosurgical instrument 200. As well known in the technical field, the S-parameter is a measure of the return loss of microwave energy due to impedance mismatch, and as such the S-parameter is indicative of the degree of impedance mismatch between the target tissue and the radiating tip. The S-parameter can be defined by the equation $P_I = SP_R$, where $P_I$ is the outgoing power in the instrument towards the tissue, $P_R$ is the power reflected back from the tissue, and S is the S-parameter. As shown in FIG. 6, the S-parameter is −17.09 dB at 5.8 GHz, meaning that very little microwave energy was reflected back from the tissue at this frequency. This indicates a good impedance match at the operating frequency of 5.8 GHz, and that microwave energy is efficiently delivered from the radiating tip into the tissue at this frequency.

The inventors carried out ex-vivo testing of an electrosurgical instrument having a structure similar to that illustrated in FIGS. 2 and 3. The tests were carried out using morbid porcine tissue (liver destined for the food chain). The samples were sealed in a bag and placed in a water bath at 37° C. prior to testing. The distal end of the electrosurgical instrument was then inserted into the prepared tissue samples. RF and microwave energy was then delivered to the samples. The RF energy had a frequency of 400 kHz and a 18 W coagulation waveform, applied for 66 s with a 918 duty cycle. The microwave energy had a frequency of 5.8 GHZ and a power level of 25 W, applied as a continuous wave for 120 s.

Measurements of the resulting ablation zones were then carried out, the results of which are shown in Table 1. The length of the ablation zone corresponds to its measured length in the longitudinal direction of the electrosurgical instrument. The width of the ablation zone corresponds to its width in a direction normal to the longitudinal direction. It was found that the shapes and sizes of the ablation zones correlate well with the simulated radiation profiles discussed above.

TABLE 1

| | Size of ablation zone | | | | |
|---|---|---|---|---|---|
| Ablation | Sample 1 | Sample 2 | Sample 3 | Sample 4 | Sample 5 |
| RF | 14 mm × 4 mm | 13 mm × 4 mm | 14 mm × 4 mm | 13 mm × 4 mm | 14 mm × 4 mm |
| Microwave | 21 mm × 16 mm | 21 mm × 16 mm | 21 mm × 15 mm | 21 mm × 14 mm | 21 mm × 15 mm |

The invention claimed is:

1. An electrosurgical instrument comprising:
a coaxial feed cable for conveying microwave energy and radiofrequency energy, the coaxial feed cable having an inner conductor, an outer conductor, and a dielectric material separating the inner conductor and the outer conductor; and
a radiating tip disposed at a distal end of the coaxial cable to receive the microwave energy and the radiofrequency energy, the radiating tip comprising:
a longitudinally extending dielectric body;
a distal electrode and a proximal electrode disposed on a surface of the dielectric body, wherein the distal electrode and the proximal electrode are physically separated from each other in the longitudinal direction by an intermediate portion of the longitudinally extending dielectric body; and
a tuning element mounted in the intermediate portion of the longitudinally extending dielectric body to enable both effective bipolar radiofrequency ablation and/or coagulation and microwave ablation,
wherein the distal electrode is electrically connected to the inner conductor,
wherein the proximal electrode is electrically connected to the outer conductor,
wherein the distal electrode and the proximal electrode are configured as an active electrode and a return electrode for delivering the radiofrequency energy to perform bipolar radiofrequency ablation or coagulation,
wherein the radiating tip is operable as an antenna for emitting the microwave energy to perform microwave ablation, wherein the distal electrode and the proximal electrode act as radiating elements of the antenna, and
wherein the electrosurgical instrument is connected to receive the microwave energy and the radiofrequency energy from an electrosurgical generator.

2. The electrosurgical instrument according to claim 1, wherein the distal electrode includes a first conductive ring on the surface of the dielectric body.

3. The electrosurgical instrument according to claim 1, wherein the proximal electrode includes a second conductive ring on the surface of the dielectric body, and wherein the inner conductor is connected to the distal electrode via a conductor that passes through the second conductive ring.

4. The electrosurgical instrument according to claim 1, wherein the proximal electrode and the distal electrode have the same dimensions.

5. The electrosurgical instrument according to claim 1, wherein the outer conductor terminates at the proximal electrode.

6. The electrosurgical instrument according to claim 1, wherein the inner conductor extends through the dielectric body, and wherein the inner conductor is electrically connected to the distal electrode by a conductive connection element that extends radially from the inner conductor.

7. The electrosurgical instrument according to claim 1, wherein the tuning element comprises an electrically conductive body mounted within the intermediate portion of the dielectric body, the electrically conductive body being electrically connected to the inner conductor.

8. The electrosurgical instrument according to claim 7, wherein the electrically conductive body is a sleeve mounted around a portion of the inner conductor that extends into the dielectric body.

9. The electrosurgical instrument according to claim 1, wherein the tuning element has a longitudinal length less than a longitudinal separation of the distal electrode and the proximal electrode.

10. The electrosurgical instrument according to claim 1, wherein the dielectric body comprises a protruding portion of the dielectric material that extends beyond a distal end of the outer conductor.

11. The electrosurgical instrument according to claim 10, wherein the tuning element is mounted within the protruding portion of the dielectric material.

12. The electrosurgical instrument according to claim 10, wherein the intermediate portion of the longitudinally extending dielectric body comprises an electrically insulating collar mounted over the protruding portion of the dielectric material.

13. The electrosurgical instrument according to claim 1, wherein outer surfaces of the distal electrode, intermediate portion and proximal electrode are flush along the radiating tip.

14. The electrosurgical instrument according to claim 1, wherein the tuning element has dimensions selected to introduce a capacitance for improving the coupling efficiency of the antenna.

15. The electrosurgical instrument according to claim 1, wherein the radiating tip further includes a dielectric choke.

16. An electrosurgical system for treating biological tissue, the system comprising:
the electrosurgical instrument according to claim 1 connected to receive the microwave energy and the radiofrequency energy from the electrosurgical generator;
the electrosurgical generator arranged to supply the microwave energy and the radiofrequency energy; and
a surgical scoping device having a flexible insertion cord for insertion into a patient's body, wherein the flexible insertion cord has an instrument channel running along its length, and wherein the electrosurgical instrument is dimensioned to fit within the instrument channel.

17. An electrosurgical instrument for treating biological tissue, the system comprising:
- the electrosurgical instrument according to claim 1 connected to receive the microwave energy and the radiofrequency energy from the electrosurgical generator; and
- the electrosurgical generator arranged to supply the microwave energy and the radiofrequency energy, wherein the electrosurgical generator is configured to switch between supplying the radiofrequency energy and supplying the microwave energy.

* * * * *